United States Patent [19]
Bandman et al.

[11] Patent Number: 5,821,086
[45] Date of Patent: Oct. 13, 1998

[54] HUMAN GLYCOPROTEIN

[75] Inventors: Olga Bandman, Mountain View; Janice Au-Young, Berkeley; Phillip R. Hawkins, Mountain View; Jennifer L. Hillman, San Jose, all of Calif.

[73] Assignee: Incyte Pharmaceuticals, Inc., Palo Alto, Calif.

[21] Appl. No.: 695,355

[22] Filed: Aug. 9, 1996

[51] Int. Cl.[6] .......................... C12P 21/06; C12N 15/00; C07K 1/00; C07H 21/04
[52] U.S. Cl. ...................... 435/69.3; 435/320.1; 435/325; 435/69.1; 435/252.3; 530/350; 536/23.5
[58] Field of Search .......................... 536/23.5; 530/350; 435/320.1, 325, 69.1, 69.3, 252.3

[56] References Cited

PUBLICATIONS

Lazar et al (Molecular & Cellular Bio. vol. 8 pp. 1247–1252), Mar. 1988.
Burgess et al (J. of Cell Bio. vol. 111 pp. 2129–2138), Nov. 1990.
Salgaller et al (Cancer. Immuno. Immunother. vol. 39 pp. 105–116), 1994.
Hillier, L. et al., (GI 1383424) EMBL Database (Accession W73289), National Center for Biotechnology Information, National Library of Medicine, Bethesda, Maryland, 20894 Oct. 16, 1996.
Hillier, L. et al., (GI 1312668) EMBL Database (Accession W31677), National Center for Biotechnology Information, National Library of Medicine, Bethesda, Maryland, 20894 Oct. 10, 1996
Johnston, I.G., et al., "Molecular Cloning of a Novel mRNA Using an Antibody Directed Against Synaptic Glycoproteins" *J. Neurosci. Res.*, 32:159–166 (1992) (GI 256933).
Sudhof, T.C., "The synaptic vesicle cycle: a cascade of protein–protein interactions" *Nature*, 375:645–653 (1995).
Bennett, M.K., et al., "Molecular correlates of synaptic vesicle docking and fusion" *Curr. Opin. Neurobiol.*, 4:324–329 (1994).
Nosten–Bertrand, M., et al., "Normal spatial learning despite regional inhibition of LTP in mice lacking Thy–1" *Nature*, 379:826–829 (1996).
Zhong, Y., et al., "Altered Nerve Terminal Arborization and Synaptic Transmission in Drosophila Mutants of Cell Adhesion Molecule Fasciclin I" *J. Neurosci.*, 15:6679–6687 (1995).
Rose, S.P., "How chicks make memories: the cellular cascade from c–fos to dendritic remodelling" *Trends Neurosci.*, 14:390–397 (1991).
Mileusnic, R., et al., "Characterisation of Antibodies Specific for Chick Brain Neural Cell Adhesion Molecules Which Cause Amnesia for a Passive Aviodance Task" *J. Neurochem.*, 64:2598–2606 (1995).
Soulliere, J., et al., "Tyrosine Phosphorylation of Glycoproteins in the Adult and Developing Rat Brain" *J. Neurosci. Res.*, 37:506–514 (1994).
Boss, B.J., et al., *Pathophysiology*, Library/Media Center, Westminster, Co, McCance and Huether eds, 527–586 (1994).
Lassmann, H., et al., "Synaptic Pathology of Alzheimer's Disease" *Ann NY Acad. Sci.*, 995:59–64 (1993).
Andre, B., et al., (GI 1077162), GenBank Sequence Database (Accession 1077162), National Center for Biotechnology Information, National Library of Medicine, Bethesda, Maryland 20894.

*Primary Examiner*—Anthony C. Caputa
*Assistant Examiner*—Mark Nauarro
*Attorney, Agent, or Firm*—Lucy J. Billings; Incyte Pharmaceuticals

[57] ABSTRACT

The present invention provides polynucleotides which identify and encode a novel human glycoprotein (SC2H). The invention provides for genetically engineered expression vectors and host cells comprising the nucleic acid sequence encoding SC2H. The invention also provides for the use of substantially purified SC2H and its agonists in the commercial production of recombinant proteins for the treatment of diseases associated with the expression of SC2H. Additionally, the invention provides for the use of antisense molecules to SC2H in the treatment of diseases associated with the expression of SC2H. The invention also describes diagnostic assays which utilize diagnostic compositions comprising the polynucleotides which hybridize with naturally occurring sequences encoding SC2H and antibodies which specifically bind to the protein.

6 Claims, 6 Drawing Sheets

```
5'  A TCG CTG CGG TTG CGA GCG CTG TAG GGA GCC TGT GCT GTG CCG CGC AGT TAG
         9       18      27      36      45      54

GCA GCA GCC GCG GAG CAG TAG CCG CCC TGG GAG GGA GCC ATG AAG CAT TAC
         63      72      81      90      99      108
    M   K   H   Y

GAG GTG GAG ATT CTG GAC GCA AAG ACA AGG GAG AAG CTG TGT TTC TTG GAC AAG
         117     126     135     144     153     162
    E   V   E   I   L   D   A   K   T   R   E   K   L   C   F   L   D   K

GTG GAG CCC CAC GCC ACC ATT GCG GAG ATC AAG AAC CTC TTC ACT AAG ACC CAT
         171     180     189     198     207     216
    V   E   P   H   A   T   I   A   E   I   K   N   L   F   T   K   T   H

CCG CAG TGG TAC CCC GCC CGC CAG TCC CTC CGC CTG GAC CCC AAG GGC AAG TCC
         225     234     243     252     261     270
    P   Q   W   Y   P   A   R   Q   S   L   R   L   D   P   K   G   K   S

CTG AAG GAT GAG GAT GTT CTG CAG AAG CTG CCC GTG GGC ACC ACG GCC ACA CTG
         279     288     297     306     315     324
    L   K   D   E   D   V   L   Q   K   L   P   V   G   T   T   A   T   L

TAC TTC CGG GAC CTG GGG GCC CAG ATC AGC TGG GTG ACG GTC TTC CTA ACA GAG
         333     342     351     360     369     378
    Y   F   R   D   L   G   A   Q   I   S   W   V   T   V   F   L   T   E

FIGURE 1A
```

```
            387         396         405         414         423         432
    TAC GCG NGG CCC CTT TTC ATC TAC CTG CTC TTC TAC TTC CGA GTG CCC TTC ATC
     Y   A   X   P   L   F   I   Y   L   L   F   Y   F   R   V   P   F   I 441         450         459         468         477         486
    TAT GGC CAC AAA TAT GAC TTT ACG TCC AGT CGG CAT ACA GTG GTG CAC CTC GCC
     Y   G   H   K   Y   D   F   T   S   S   R   H   T   V   V   H   L   A 495         504         513         522         531         540
    TGC ATC TGT CAC TCA TTC CAC TAC ATC AAG CGC CTG CTG GAG ACG CTC TTC GTG
     C   I   C   H   S   F   H   Y   I   K   R   L   L   E   T   L   F   V 549         558         567         576         585         594
    CAC CGC TTC TCC CAT GGC ACT ATG CCT TTG CGC AAC ATC TTC AAG AAC TGC ACC
     H   R   F   S   H   G   T   M   P   L   R   N   I   F   K   N   C   T 603         612         621         630         639         648
    TAC TAC TGG GGC TTC GCC GCG ATG GCC TAT TAC ATC AAT CAC CCT CTC TAC
     Y   Y   W   G   F   A   A   M   A   Y   Y   I   N   H   P   L   Y 657         666         675         684         693         702
    ACT CCC CCT ACC TAC GGA GCT CAG CAG GTG AAA CTG GCG CTC GCC ATC TTT GTG
     T   P   P   T   Y   G   A   Q   Q   V   K   L   A   L   A   I   F   V 711         720         729         738         747         756
    ATC TGC CAG CTC GGC AAC TTC TCC ATC CAC ATG GCC CTG CGG GAC CTG CGG CCC
     I   C   Q   L   G   N   F   S   I   H   M   A   L   R   D   L   R   P
```

FIGURE 1B

```
         765            774            783            792            801            810
GCT GGG TCC AAG ACG CGG AAG ATC CCA TAC CCC ACC AAG AAC CCC TTC ACG TGG
 A   G   S   K   T   R   K   I   P   Y   P   T   K   N   P   F   T   W 819            828            837            846            855            864
CTC NTT CTG CTG GTG TCC TGC CCC AAC TAC ACC TAC GAG GTG GGG TCC TGG ATC
 L   X   L   L   V   S   C   P   N   Y   T   Y   E   V   G   S   W   I 873            882            891            900            909            918
GGT TTC GCC ATC ATG ACC ACG CAG TGT CTC CCA GTG GCC CTG TTC TCC CTG GTG GGC
 G   F   A   I   M   T   T   Q   C   L   P   V   A   L   F   S   L   V   G 927            936            945            954            963            972
TTC ACC CAG ATG ACC ATC TGG GCC AAG GGC AAG CAC CGC AGC TAC CTG AAG GAG
 F   T   Q   M   T   I   W   A   K   G   K   H   R   S   Y   L   K   E 981            990            999           1008           1017           1026
TTC CGG GAC TAC CCG CCC CTG CGC ATG CCC ATG ATC CCC TTC CTG CTC TGA GCG
 F   R   D   Y   P   P   L   R   M   P   M   I   P   F   L   L   *

1035           1044           1053           1062           1071           1080
CTC ACC CCT GCT GAG GCT CAG CCC CTC AAC CCG GTG GCA TTC TGG GGG AGG AGT 1089           1098           1107           1116           1125           1134
GGG GCC CAC AGC TCT CCA GCA CCC GGA ATA AAG CCC GCC TGC CCC AGT CGG AAA

AAA AA 3'
```

FIGURE 1C

```
     MKHYEVEILDAKTREKLCFLDKVEPHATIAEI--KNLFTKT         SC2H
  1  MKHYEVEIRDAKTREKLCFLDKVEPQATISEI--KTLFTKT         GI 256993
  1  M-PITIKSRSKGLRDTEIDLSK---KPTLDDVLKKISANN          GI 1077162

40  HPQW--YPARQSLRLDPKGKSLKDEDVLQKLPVGTTATLYF         SC2H
 40  HPQW--YPARQSLRLDPKGKSLKDEDVLQKLPVGTTATLYF         GI 256993
 37  HNISKYRIRLTYKKESKQVPVISEFFQE-EADDSMEFFI           GI 1077162

79  RDLGAQISWVTVFLTEYAXPLFIYLLFYF--RVPFIYGHK          SC2H
 79  RDLGAQISWVTVFLTEYAGPLFIYLLFYF--RVPFIYGRK          GI 256993
 76  KDLGPQISWRLVFFCEYLGPVLVHSLFYYLSTIPTVVDRW          GI 1077162

117  Y---DFTSSRHTVVHLACICHSFHYIKRLLETLFVHRFS           SC2H
117  Y---DFTSSRHTVVHLACMCHSFHYIKRLLETLFVHRFS           GI 256993
116  HSASSDYNPFLNRVAYFLILGH--YGKRLFETLFVHQFS           GI 1077162

153  HGTMPLRNIFKNCTYYWGFAAWMAY----YINHPLY              SC2H
153  HGTMPLRNIFKNCTYYWGFAAWMAY----YINHPLY              GI 256993
153  LATMPIFNLFKNCFHYWVLSGLISFGYFGYGFPFGNAKLF          GI 1077162

185  TPPTY--GAQQVKLALAIFVICQLGNFSIHMALRDLRPAGS         SC2H
185  TPPTY--GVQQVKLALAIFVICQLGNFSIHMALRDLRPAGS         GI 256993
193  KYYSYLKDDLSTLIGLFVLSELWNFYCHIKLR-LWGDYQ           GI 1077162
```

FIGURE 2A

```
224 KTR---KIPYPTKNPFTWLXLLVSCPNYTYEVGSWIGFAI    SC2H
224 KTR---KIPYPTKNPFTWLFLLVSCPNYTYEVGSWIGFAI    GI 256993
232 KKHGNAKIRVPLNQG---IFNLFVAPNYTFEVWSIWFTF     GI 1077162

261 MTQC-LPVALFSLVGFTQMTIWAKGKHRSYLKEFRDYPPL    SC2H
261 MTQC-VPVALFSLVGFTQMTIWAKGKHRSYLKEFRDYPPL    GI 256993
269 VFKFNLFAVLFLTVSTAQMYAWAQKKNKKYHTR-RAF--     GI 1077162

300 RMPIIPFLL                                   SC2H
300 RMPIIPFLL                                   GI 256993
305 ---LIPFVF                                   GI 1077162
```

FIGURE 2B

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:

( A ) LENGTH: 308 amino acids ( B ) TYPE: amino acid ( C ) STRANDEDNESS: single
            ( D ) TOPOLOGY: linear ( i i ) MOLECULE TYPE: peptide ( v i i ) IMMEDIATE SOURCE:
            ( A ) LIBRARY: BRAINOT03
            ( B ) CLONE: 659029

( x i ) SEQUENCE DESCRIPTION: SEQ ID NO:1:

| Met | Lys | His | Tyr | Glu | Val | Glu | Ile | Leu | Asp | Ala | Lys | Thr | Arg | Glu | Lys |
|---|---|---|---|---|---|---|---|---|---|---|---|---|---|---|---|
| 1 | | | | 5 | | | | | 10 | | | | | 15 | |

| Leu | Cys | Phe | Leu | Asp | Lys | Val | Glu | Pro | His | Ala | Thr | Ile | Ala | Glu | Ile |
|---|---|---|---|---|---|---|---|---|---|---|---|---|---|---|---|
| | | | 20 | | | | | 25 | | | | | 30 | | |

| Lys | Asn | Leu | Phe | Thr | Lys | Thr | His | Pro | Gln | Trp | Tyr | Pro | Ala | Arg | Gln |
|---|---|---|---|---|---|---|---|---|---|---|---|---|---|---|---|
| | | 35 | | | | | 40 | | | | | 45 | | | |

| Ser | Leu | Arg | Leu | Asp | Pro | Lys | Gly | Lys | Ser | Leu | Lys | Asp | Glu | Asp | Val |
|---|---|---|---|---|---|---|---|---|---|---|---|---|---|---|---|
| | 50 | | | | | 55 | | | | | 60 | | | | |

| Leu | Gln | Lys | Leu | Pro | Val | Gly | Thr | Thr | Ala | Thr | Leu | Tyr | Phe | Arg | Asp |
|---|---|---|---|---|---|---|---|---|---|---|---|---|---|---|---|
| 65 | | | | | 70 | | | | | 75 | | | | | 80 |

| Leu | Gly | Ala | Gln | Ile | Ser | Trp | Val | Thr | Val | Phe | Leu | Thr | Glu | Tyr | Ala |
|---|---|---|---|---|---|---|---|---|---|---|---|---|---|---|---|
| | | | | 85 | | | | | 90 | | | | | 95 | |

| Xaa | Pro | Leu | Phe | Ile | Tyr | Leu | Leu | Phe | Tyr | Phe | Arg | Val | Pro | Phe | Ile |
|---|---|---|---|---|---|---|---|---|---|---|---|---|---|---|---|
| | | | 100 | | | | | 105 | | | | | 110 | | |

| Tyr | Gly | His | Lys | Tyr | Asp | Phe | Thr | Ser | Ser | Arg | His | Thr | Val | Val | His |
|---|---|---|---|---|---|---|---|---|---|---|---|---|---|---|---|
| | | 115 | | | | | 120 | | | | | 125 | | | |

| Leu | Ala | Cys | Ile | Cys | His | Ser | Phe | His | Tyr | Ile | Lys | Arg | Leu | Leu | Glu |
|---|---|---|---|---|---|---|---|---|---|---|---|---|---|---|---|
| | 130 | | | | | 135 | | | | | 140 | | | | |

| Thr | Leu | Phe | Val | His | Arg | Phe | Ser | His | Gly | Thr | Met | Pro | Leu | Arg | Asn |
|---|---|---|---|---|---|---|---|---|---|---|---|---|---|---|---|
| 145 | | | | | 150 | | | | | 155 | | | | | 160 |

| Ile | Phe | Lys | Asn | Cys | Thr | Tyr | Tyr | Trp | Gly | Phe | Ala | Ala | Trp | Met | Ala |
|---|---|---|---|---|---|---|---|---|---|---|---|---|---|---|---|
| | | | | 165 | | | | | 170 | | | | | 175 | |

| Tyr | Tyr | Ile | Asn | His | Pro | Leu | Tyr | Thr | Pro | Pro | Thr | Tyr | Gly | Ala | Gln |
|---|---|---|---|---|---|---|---|---|---|---|---|---|---|---|---|
| | | | 180 | | | | | 185 | | | | | 190 | | |

| Gln | Val | Lys | Leu | Ala | Leu | Ala | Ile | Phe | Val | Ile | Cys | Gln | Leu | Gly | Asn |
|---|---|---|---|---|---|---|---|---|---|---|---|---|---|---|---|
| | | 195 | | | | | 200 | | | | | 205 | | | |

| Phe | Ser | Ile | His | Met | Ala | Leu | Arg | Asp | Leu | Arg | Pro | Ala | Gly | Ser | Lys |
|---|---|---|---|---|---|---|---|---|---|---|---|---|---|---|---|
| | 210 | | | | | 215 | | | | | 220 | | | | |

| Thr | Arg | Lys | Ile | Pro | Tyr | Pro | Thr | Lys | Asn | Pro | Phe | Thr | Trp | Leu | Xaa |
|---|---|---|---|---|---|---|---|---|---|---|---|---|---|---|---|
| 225 | | | | | 230 | | | | | 235 | | | | | 240 |

| Leu | Leu | Val | Ser | Cys | Pro | Asn | Tyr | Thr | Tyr | Glu | Val | Gly | Ser | Trp | Ile |
|---|---|---|---|---|---|---|---|---|---|---|---|---|---|---|---|
| | | | | 245 | | | | | 250 | | | | | 255 | |

| Gly | Phe | Ala | Ile | Met | Thr | Gln | Cys | Leu | Pro | Val | Ala | Leu | Phe | Ser | Leu |
|---|---|---|---|---|---|---|---|---|---|---|---|---|---|---|---|
| | | | | 260 | | | | | 265 | | | | | 270 | |

| Val | Gly | Phe | Thr | Gln | Met | Thr | Ile | Trp | Ala | Lys | Gly | Lys | His | Arg | Ser |
|---|---|---|---|---|---|---|---|---|---|---|---|---|---|---|---|
| | | 275 | | | | | 280 | | | | | 285 | | | |

| Tyr | Leu | Lys | Glu | Phe | Arg | Asp | Tyr | Pro | Pro | Leu | Arg | Met | Pro | Ile | Ile |
|---|---|---|---|---|---|---|---|---|---|---|---|---|---|---|---|
| | 290 | | | | | 295 | | | | | 300 | | | | |

| Pro | Phe | Leu | Leu |
|---|---|---|---|
| 305 | | | |

( 2 ) INFORMATION FOR SEQ ID NO:2:

( i ) SEQUENCE CHARACTERISTICS:
            ( A ) LENGTH: 1137 base pairs
            ( B ) TYPE: nucleic acid
            ( C ) STRANDEDNESS: single
            ( D ) TOPOLOGY: linear ( i i ) MOLECULE TYPE: cDNA ( v i i ) IMMEDIATE SOURCE:
    ( A ) LIBRARY: BRAINOT03
    ( B ) CLONE: 659029

( x i ) SEQUENCE DESCRIPTION: SEQ ID NO:2:

| | | | | | | |
|---|---|---|---|---|---|---|
| ATCGCTGCGG | TTGCGAGCGC | TGTAGGGAGC | CTGTGCTGTG | CCGCGCAGTT | AGGCAGCAGC | 60 |
| AGCCGCGGAG | CAGTAGCCGC | CGTGGGAGGG | AGCCATGAAG | CATTACGAGG | TGGAGATTCT | 120 |
| GGACGCAAAG | ACAAGGGAGA | AGCTGTGTTT | CTTGGACAAG | GTGGAGCCCC | ACGCCACCAT | 180 |
| TGCGGAGATC | AAGAACCTCT | TCACTAAGAC | CCATCCGCAG | TGGTACCCCG | CCCGCCAGTC | 240 |
| CCTCCGCCTG | GACCCCAAGG | GCAAGTCCCT | GAAGGATGAG | GATGTTCTGC | AGAAGCTGCC | 300 |
| CGTGGGCACC | ACGGCCACAC | TGTACTTCCG | GGACCTGGGG | GCCCAGATCA | GCTGGGTGAC | 360 |
| GGTCTTCCTA | ACAGAGTACG | CGNGGCCCCT | TTTCATCTAC | CTGCTCTTCT | ACTTCCGAGT | 420 |
| GCCCTTCATC | TATGGCCACA | AATATGACTT | TACGTCCAGT | CGGCATACAG | TGGTGCACCT | 480 |
| CGCCTGCATC | TGTCACTCAT | TCCACTACAT | CAAGCGCCTG | CTGGAGACGC | TCTTCGTGCA | 540 |
| CCGCTTCTCC | CATGGCACTA | TGCCTTTGCG | CAACATCTTC | AAGAACTGCA | CCTACTACTG | 600 |
| GGGCTTCGCC | GCGTGGATGG | CCTATTACAT | CAATCACCCT | CTCTACACTC | CCCTACCTA | 660 |
| CGGAGCTCAG | CAGGTGAAAC | TGGCGCTCGC | CATCTTTGTG | ATCTGCCAGC | TCGGCAACTT | 720 |
| CTCCATCCAC | ATGGCCCTGC | GGGACCTGCG | GCCCGCTGGG | TCCAAGACGC | GGAAGATCCC | 780 |
| ATACCCCACC | AAGAACCCCT | TCACGTGGCT | CNTTCTGCTG | GTGTCCTGCC | CCAACTACAC | 840 |
| CTACGAGGTG | GGGTCCTGGA | TCGGTTTCGC | CATCATGACG | CAGTGTCTCC | CAGTGGCCCT | 900 |
| GTTCTCCCTG | GTGGGCTTCA | CCCAGATGAC | CATCTGGGCC | AAGGGCAAGC | ACCGCAGCTA | 960 |
| CCTGAAGGAG | TTCCGGGACT | ACCCGCCCCT | GCGCATGCCC | ATCATCCCT | TCCTGCTCTG | 1020 |
| AGCGCTCACC | CCTGCTGAGG | CTCAGCCCCT | CAACCCGGTG | GCATTCTGGG | GGAGGAGTGG | 1080 |
| GGCCCACAGC | TCTCCAGCAC | CCGGAATAAA | GCCCGCCTGC | CCCAGTCGGA | AAAAAA | 1137 |

( 2 ) INFORMATION FOR SEQ ID NO:3:

( i ) SEQUENCE CHARACTERISTICS:
        ( A ) LENGTH: 308 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: GenBank
        ( B ) CLONE: 256993

( x i ) SEQUENCE DESCRIPTION: SEQ ID NO:3:

```
Met Lys His Tyr Glu Val Glu Ile Arg Asp Ala Lys Thr Arg Glu Lys
 1               5                  10                  15

Leu Cys Phe Leu Asp Lys Val Glu Pro Gln Ala Thr Ile Ser Glu Ile
            20                  25                  30

Lys Thr Leu Phe Thr Lys Thr His Pro Gln Trp Tyr Pro Ala Arg Gln
        35                  40                  45

Ser Leu Arg Leu Asp Pro Lys Gly Lys Ser Leu Lys Asp Glu Asp Val
    50                  55                  60

Leu Gln Lys Leu Pro Val Gly Thr Thr Ala Thr Leu Tyr Phe Arg Asp
65                  70                  75                  80

Leu Gly Ala Gln Ile Ser Trp Val Thr Val Phe Leu Thr Glu Tyr Ala
                85                  90                  95
```

```
Gly  Pro  Leu  Phe  Ile  Tyr  Leu  Leu  Phe  Tyr  Phe  Arg  Val  Pro  Phe  Ile
               100                      105                      110

Tyr  Gly  Arg  Lys  Tyr  Asp  Phe  Thr  Ser  Ser  Arg  His  Thr  Val  Val  His
          115                      120                      125

Leu  Ala  Cys  Met  Cys  His  Ser  Phe  His  Tyr  Ile  Lys  Arg  Leu  Leu  Glu
     130                      135                      140

Thr  Leu  Phe  Val  His  Arg  Phe  Ser  His  Gly  Thr  Met  Pro  Leu  Arg  Asn
145                      150                      155                      160

Ile  Phe  Lys  Asn  Cys  Thr  Tyr  Tyr  Trp  Gly  Phe  Ala  Ala  Trp  Met  Ala
               165                      170                      175

Tyr  Tyr  Ile  Asn  His  Pro  Leu  Tyr  Thr  Pro  Pro  Thr  Tyr  Gly  Val  Gln
               180                      185                      190

Gln  Val  Lys  Leu  Ala  Leu  Ala  Ile  Phe  Val  Ile  Cys  Gln  Leu  Gly  Asn
          195                      200                      205

Phe  Ser  Ile  His  Met  Ala  Leu  Arg  Asp  Leu  Arg  Pro  Ala  Gly  Ser  Lys
     210                      215                      220

Thr  Arg  Lys  Ile  Pro  Tyr  Pro  Thr  Lys  Asn  Pro  Phe  Thr  Trp  Leu  Phe
225                      230                      235                      240

Leu  Leu  Val  Ser  Cys  Pro  Asn  Tyr  Thr  Tyr  Glu  Val  Gly  Ser  Trp  Ile
               245                      250                      255

Gly  Phe  Ala  Ile  Met  Thr  Gln  Cys  Val  Pro  Val  Ala  Leu  Phe  Ser  Leu
               260                      265                      270

Val  Gly  Phe  Thr  Gln  Met  Thr  Ile  Trp  Ala  Lys  Gly  Lys  His  Arg  Ser
          275                      280                      285

Tyr  Leu  Lys  Glu  Phe  Arg  Asp  Tyr  Pro  Pro  Leu  Arg  Met  Pro  Ile  Ile
     290                      295                      300

Pro  Phe  Leu  Leu
305
```

(2) INFORMATION FOR SEQ ID NO:4:

(i) SEQUENCE CHARACTERISTICS:
        (A) LENGTH: 310 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 1077162

(xi) SEQUENCE DESCRIPTION: SEQ ID NO:4:

```
Met  Pro  Ile  Thr  Ile  Lys  Ser  Arg  Ser  Lys  Gly  Leu  Arg  Asp  Thr  Glu
1                        5                        10                       15

Ile  Asp  Leu  Ser  Lys  Lys  Pro  Thr  Leu  Asp  Asp  Val  Leu  Lys  Lys  Ile
               20                       25                       30

Ser  Ala  Asn  Asn  His  Asn  Ile  Ser  Lys  Tyr  Arg  Ile  Arg  Leu  Thr  Tyr
          35                       40                       45

Lys  Lys  Glu  Ser  Lys  Gln  Val  Pro  Val  Ile  Ser  Glu  Ser  Phe  Phe  Gln
     50                       55                       60

Glu  Glu  Ala  Asp  Asp  Ser  Met  Glu  Phe  Phe  Ile  Lys  Asp  Leu  Gly  Pro
65                       70                       75                       80

Gln  Ile  Ser  Trp  Arg  Leu  Val  Phe  Phe  Cys  Glu  Tyr  Leu  Gly  Pro  Val
               85                       90                       95

Leu  Val  His  Ser  Leu  Phe  Tyr  Tyr  Leu  Ser  Thr  Ile  Pro  Thr  Val  Val
               100                      105                      110
```

| | | | | | | | | | | | | | | |
|---|---|---|---|---|---|---|---|---|---|---|---|---|---|---|
| Asp | Arg | Trp 115 | His | Ser | Ala | Ser | Ser 120 | Asp | Tyr | Asn | Pro | Phe 125 | Leu | Asn | Arg |
| Val | Ala 130 | Tyr | Phe | Leu | Ile | Leu 135 | Gly | His | Tyr | Gly | Lys 140 | Arg | Leu | Phe | Glu |
| Thr 145 | Leu | Phe | Val | His | Gln 150 | Phe | Ser | Leu | Ala | Thr 155 | Met | Pro | Ile | Phe | Asn 160 |
| Leu | Phe | Lys | Asn | Cys 165 | Phe | His | Tyr | Trp | Val 170 | Leu | Ser | Gly | Leu | Ile 175 | Ser |
| Phe | Gly | Tyr | Phe 180 | Gly | Tyr | Gly | Phe | Pro 185 | Phe | Gly | Asn | Ala | Lys 190 | Leu | Phe |
| Lys | Tyr | Tyr 195 | Ser | Tyr | Leu | Lys | Leu 200 | Asp | Asp | Leu | Ser | Thr 205 | Leu | Ile | Gly |
| Leu | Phe 210 | Val | Leu | Ser | Glu | Leu 215 | Trp | Asn | Phe | Tyr | Cys 220 | His | Ile | Lys | Leu |
| Arg 225 | Leu | Trp | Gly | Asp | Tyr 230 | Gln | Lys | Lys | His | Gly 235 | Asn | Ala | Lys | Ile | Arg 240 |
| Val | Pro | Leu | Asn | Gln 245 | Gly | Ile | Phe | Asn | Leu 250 | Phe | Val | Ala | Pro | Asn 255 | Tyr |
| Thr | Phe | Glu | Val 260 | Trp | Ser | Trp | Ile | Trp 265 | Phe | Thr | Phe | Val | Phe 270 | Lys | Phe |
| Asn | Leu | Phe 275 | Ala | Val | Leu | Phe | Leu 280 | Thr | Val | Ser | Thr | Ala 285 | Gln | Met | Tyr |
| Ala | Trp 290 | Ala | Gln | Lys | Lys | Asn 295 | Lys | Lys | Tyr | His | Thr 300 | Arg | Arg | Ala | Phe |
| Leu 305 | Ile | Pro | Phe | Val | Phe 310 | | | | | | | | | | |

HUMAN GLYCOPROTEIN

FIELD OF THE INVENTION

The present invention relates to nucleic acid and amino acid sequences of a novel human glycoprotein and to the use of these sequences in the diagnosis, study, prevention and treatment of disease.

BACKGROUND OF THE INVENTION

SC2 is a 308 residue glycoprotein highly expressed in neuronal-enriched regions of the rat central nervous system (CNS). The SC2 sequence has an unglycosylated molecular mass of 36.1 kdal and contains a putative membrane-spanning domain located near the carboxy terminus (Johnston IG et al (1992) J Neurosci Res 32:159–166). All three potential N-linked glycosylation sites are on the amino-terminal side of the membrane-spanning domain. Two tyrosine residues are present on the carboxy-terminal side of the transmembrane domain. SC2 mRNA is present throughout postnatal cerebellar development. The highest levels of SC2 expression are found in neuronal cell types, including pyramidal cells of the hippocampus, all layers of the neocortex, granule, and Purkinje neurons of the cerebellum. SC2 is also expressed at low levels in many other tissues.

Glycoproteins participate in the mechanisms of neurotransmitter release. The tightly-regulated synaptic vesicle cycle at the nerve terminal consists of the formation of synaptic vesicles, the docking of vesicles to the presynaptic plasma membrane, the fusion of these membranes and consequent neurotransmitter release, endocytosis of the empty vesicles and the regeneration of fresh vesicles. A variety of glycoproteins are involved in these processes, serving as recognition and/or adhesion molecules (reviewed in Sudhof TC (1995) Nature 375:645–653; Bennet MK and RH Scheller (1994) Curr Opin Neurobiol 4:324–329).

Glycoproteins present in the synapses of the mammalian CNS play a major role in the establishment and in the adhesive stability of synaptic contacts and in neuronal functioning. Synaptic modifications induced by learning and long-term potentiation (LTP) may involve the action of cell adhesion molecules, which include a variety of neuronal glycoproteins (Nosten-Bertrand M et al (1996) Nature 379:826–829). Cell adhesion glycoprotein molecules are involved in target recognition and synaptogenesis at neuromuscular junctions, and may play a role in fine-tuning nerve terminal arborization and in modifying the development of presynaptic functions. Defects in fasciclin I (Fas I), an insect glycoprotein expressed in motor nerve axons and terminals, result in defective presynaptic function (Zhong Y and Shanley J (1995) J Neurosci 15:6679–6687).

The processes of learning and memory establishment involve the glycoprotein-mediated structural remodeling and stabilization of synapses. Training chicks in a one-trial passive avoidance task results in a cellular cascade which includes 1) phosphorylation of the presynaptic protein kinase C substrate B-50, 2) increased synthesis of pre- and postsynaptic glycoproteins, 3) subsequent increases in dendritic spine densities, synapse and synaptic vesicle numbers, and 4) prolonged increase in neuronal bursting (Rose SP (1991) Trends Neurosci 14:390–397).

Glycoprotein-associated effects are regulated by post-translational modifications, such as variations in the structure of attached carbohydrate moieties and in phosphorylation. For example, certain synaptic glycoproteins show enhanced fucosylation in day-old chicks subjected to a passive-avoidance task. Antibodies directed against these glycoproteins cause a loss of memory of this learned response (Mileusnic R et al (1995) J Neurochem 64:2598–2606). Tyrosine phosphorylation of neuronal glycoproteins paralleling synaptic formation suggests a role for these glycoproteins in synapse development and in signal transduction (Soulliere J et al (1994) J Neurosci Res 37:506–514).

Neuronal atrophy and synapse loss has been correlated with numerous neurodegenerative disorders. The severity of Parkinson disease correlates with the degree of neuronal loss in the substantia nigra. The principal pathologic feature of Huntington disease is severe degeneration of the basal ganglia, which contain a preponderance of GABA-nergic neurons. Lower and upper motor neuron degeneration is the principal pathologic feature of amyotrophic lateral sclerosis (ALS, Lou Gehrig disease) (Boss BJ et al (1994) in Pathochysioloay, McCance KL and Huether SE eds, Mosby-Year, St. Louis Mo., pp.527–586). Dementia-associated disorders also involve nerve cell atrophy and degeneration. Synapse loss in brain tissue correlates with the severity of dementia in Alzheimer's disease (Lassmann H et al (1993) Ann NY Acad Sci 695:59–64).

Viral pathogens attach to host cell surfaces by the interaction of viral envelope glycoproteins with host membrane glycoproteins. This viral attachment is the first step in the infective cycle for numerous pathogens, including those which attack the nervous system such as poliovirus, rabies, herpes simplex, and HIV. Host cell surface glycoproteins thus provide targets for the design of anti-viral therapeutics.

Glycoproteins participate in formation and maintenance of neurons and synapses and in synaptic vesicle cycling. They are implicated in the acquisition of memory and learning. Understanding the structure and function of neuronal glycoproteins will provide insight into normal neuronal and synaptic function and their physiological and pathological modifications. The selective modulation of glycoprotein expression may provide a means for the regulation and maintenance of neurons, synapses and synaptic vesicles in neurodegenerative disorders, as well as in the control of host cell invasion by viral pathogens.

SUMMARY OF THE INVENTION

The present invention discloses a novel human glycoprotein, hereinafter referred to as SC2H, having homology to the SC2 synaptic glycoprotein from rat. Accordingly, the invention features a substantially purified glycoprotein, encoded by amino acid sequence of SEQ ID NO:1, having homology to rat glycoprotein SC2.

One aspect of the invention features isolated and substantially purified polynucleotides which encode SC2H. In a particular aspect, the polynucleotide is the nucleotide sequence of SEQ ID NO:2. In addition, the invention features nucleotide sequences which hybridize under stringent conditions to SEQ ID NO:2.

The invention further relates to nucleic acid sequence encoding SC2H, oligonucleotides, peptide nucleic acids (PNA), fragments, portions or antisense molecules thereof. The present invention also relates to an expression vector which includes polynucleotide encoding SC2H and its use to transform host cells or organisms. The invention also relates to antibodies which bind specifically to the glycoprotein of SEQ ID NO:1 and to a pharmaceutical composition comprising a substantially purified glycoprotein of SEQ ID NO:1.

BRIEF DESCRIPTION OF THE FIGURES

FIGS. 1A, 1B, and 1C show the amino acid sequence (SEQ ID NO:1) and the nucleic acid sequence (SEQ ID NO:2) of the human glycoprotein SC2H, produced using MacDNAsis software (Hitachi Software Engineering Co Ltd).

FIGS. 2A and 2B show the amino acid sequence alignments among SC2H (SEQ ID NO:1), rat SC2(GI 256993; SEQ ID NO:3), and yeast SC2 (GI 1077162; SEQ ID NO:4) produced using the multisequence alignment program of DNAStar software (DNAStar Inc, Madison Wis.).

DETAILED DESCRIPTION OF THE INVENTION

Definitions

Figure 3:
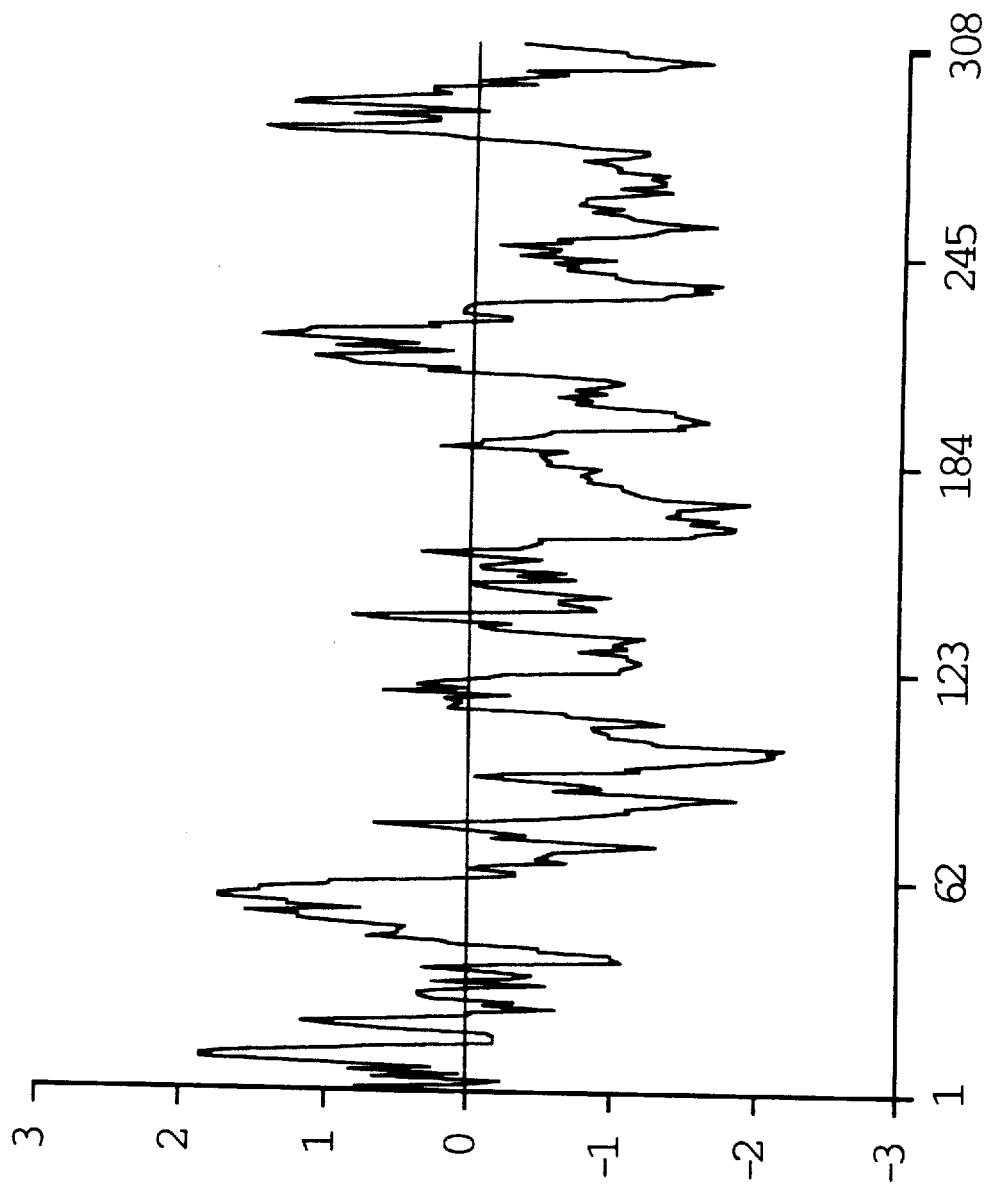
FIG. 3 shows the hydrophobicity plot (generated using MacDNAsis software) for SC2H, SEQ ID NO:1; the X axis reflects amino acid position, and the negative Y axis, hydrophobicity.

"Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, amino acid sequence as used herein refers to peptide or protein sequence.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen PE et al (1993) Anticancer Drug Des 8:53–63).

A "variant" of SC2H is defined as an amino acid sequence that is different by one or more amino acid "substitutions". The variant may have "conservative" changes, wherein a substituted amino acid has similar structural or chemical properties, eg, replacement of leucine with isoleucine. More rarely, a variant may have "nonconservative" changes, eg, replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNAStar software.

The term "biologically active" refers to an SC2H having structural, regulatory or biochemical functions of the naturally occurring SC2H. Likewise, "immunologically active" defines the capability of the natural, recombinant or synthetic SC2H, or any oligopeptide thereof, to induce a specific immune response in appropriate animals or cells and to bind with specific antibodies.

The term "derivative" as used herein refers to the chemical modification of a nucleic acid encoding SC2H or the encoded SC2H. Illustrative of such modifications would be replacement of hydrogen by an alkyl, acyl, or amino group. A nucleic acid derivative would encode a polypeptide which retains essential biological characteristics of natural SC2H.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated.

"Stringency" typically occurs in a range from about Tm–5° C. (5° C. below the Tm of the probe)to about 20° C. to 25° C. below Tm. As will be understood by those of skill in the art, a stringency hybridization can be used to identify or detect identical polynucleotide sequences or to identify or detect similar or related polynucleotide sequences.

The term "hybridization" as used herein shall include "any process by which a strand of nucleic acid joins with a complementary strand through base pairing" (Coombs J (1994) *Dictionary of Biotechnology*, Stockton Press, New York N.Y.). Amplification as carried out in the polymerase chain reaction technologies is described in Dieffenbach CW and GS Dveksler (1995, *PCR Primer, a Laboratory Manual*, Cold Spring Harbor Press, Plainview N.Y.).

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to the naturally occurring SC2H.

A "substitution" results from the replacement of one or more nucleotides or amino acids by different nucleotides or amino acids, respectively.

Description

The present invention relates to a novel human glycoprotein, SC2H, initially identified among the partial cDNAs from a human brain tissue library (BRAINOT03) and to the use of the nucleic acid and amino acid sequences disclosed herein in the study, diagnosis, prevention and treatment of disease. Northern analysis using the LIFESEQ™ database (Incyte Pharmaceuticals, Palo Alto, Calif.) indicates that SC2H-encoding nucleotide sequences are abundantly transcribed in brain and other nervous system tissues, both normal and cancerous. SC2H transcripts are highly abundant in a cDNA library prepared from brain tissue of an Alzheimer disease patient. SC2H is also transcribed in a variety of normal and cancerous tissues including prostate, lung, breast, testis, ovary, thyroid and lymphocytes.

The present invention also encompasses SC2H variants. A preferred SC2H variant is one having at least 80% amino acid sequence similarity to the SC2H amino acid sequence (SEQ ID NO:1), a more preferred SC2H variant is one having at least 90% amino acid sequence similarity to SEQ ID NO:1 and a most preferred SC2H variant is one having at least 95% amino acid sequence similarity to SEQ ID NO:1.

The nucleic acid sequence encoding a portion of SC2H was first identified in the cDNA, Incyte Clone 659029, through a computer-generated search for amino acid sequence alignments. The nucleic acid sequence, SEQ ID NO:2, disclosed herein (FIGS. 1A, 1B, and 1C) encodes the amino acid sequence, SEQ ID NO:1, designated SC2H. The present invention is based in part on the structural homology shown in FIGS. 2A and 2B, among SC2H and other glycoproteins including rat SC2 (GI 256993; Johnston, supra) and yeast SC2 (GI 1077162; Andre B et al (1995) unpublished).

SC2H consists of 308 amino acids and is a member of the class of transmembrane glycoproteins including SC2. From its homology to rat SC2 (FIG. 2), the transmembrane domain is predicted to include residues 255 to 279. SC2H has three potential N-linked glycoslyation sites, all which are on the N-terminal side of the transmembrane domain, at $N_{164}$, $N_{208}$ and $N_{247}$. The localization of the glycosylation sites suggests that the N-terminal side of the transmembrane domain is extracellular and the C-terminal side of the transmembrane domain faces the cell interior. Two tyrosines reside on the C-terminal side of the transmembrane domain at positions $Y_{289}$ and $Y_{296}$ and may serve as substrates for phosphorylation in signal transduction; $Y_{296}$, is conserved in rat SC2 and $Y_{289}$ is conserved in both the rat and yeast SC2 homologs. The human glycoprotein SC2H has 97% amino acid sequence identity to rat SC2 and 30% sequence identity to yeast SC2 (FIGS. 2A and 2B).

THE SC2H CODING SEQUENCES

The nucleic acid and amino acid sequences of SC2H are shown in FIGS. 1A, 1B, and 1C. In accordance with the invention, any nucleic acid sequence which encodes the amino acid sequence of SC2H can be used to generate recombinant molecules which express SC2H. In a specific embodiment described herein, a partial sequence of SC2H was first isolated as Incyte Clone 659029 from a human brain tissue cDNA library (BRAINOT03).

It will be appreciated by those skilled in the art that as a result of the degeneracy of the genetic code, a multitude of SC2H-encoding nucleotide sequences, some bearing minimal homology to the nucleotide sequences of any known and naturally occurring gene, may be produced. The invention contemplates each and every possible variation of nucleotide sequence that could be made by selecting combinations based on possible codon choices. These combinations are made in accordance with the standard triplet genetic code as applied to the nucleotide sequence of naturally occurring SC2H, and all such variations are to be considered as being specifically disclosed.

Although nucleotide sequences which encode SC2H and its variants are preferably capable of hybridizing to the nucleotide sequence of the naturally occurring SC2H under appropriately selected conditions of stringency, it may be advantageous to produce nucleotide sequences encoding SC2H or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding SC2H and its derivatives without altering the encoded amino acid sequences include the production of RNA transcripts having more desirable properties, such as a greater half-life, than transcripts produced from the naturally occurring sequence.

It is now possible to produce a DNA sequence, or portions thereof, encoding an SC2H and its derivatives entirely by synthetic chemistry, after which the synthetic gene may be inserted into any of the many available DNA vectors and cell systems using reagents that are well known in the art at the time of the filing of this application. Moreover, synthetic chemistry may be used to introduce mutations into a gene encoding SC2H.

Also included within the scope of the present invention are polynucleotide sequences that are capable of hybridizing to the nucleotide sequence of FIGS. 1A, 1B, and 1C under various conditions of stringency. Hybridization conditions are based on the melting temperature (Tm) of the nucleic acid binding complex or probe, as taught in Berger and Kimmel (1987, *Guide to Molecular Cloning Techniques, Methods in Enzymology*, Vol 152, Academic Press, San Diego, Calif.) incorporated herein by reference, and may be used at a defined stringency.

Altered nucleic acid sequences encoding SC2H which may be used in accordance with the invention include deletions, insertions or substitutions of different nucleotides resulting in a polynucleotide that encodes the same or a functionally equivalent SC2H. The protein may also show deletions, insertions or substitutions of amino acid residues which produce a silent change and result in a functionally equivalent SC2H. Deliberate amino acid substitutions may be made on the basis of similarity in polarity, charge, solubility, hydrophobicity, hydrophilicity, and/or the amphipathic nature of the residues as long as the biological activity of SC2H is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Included within the scope of the present invention are alleles of SC2H. As used herein, an "allele" or "allelic sequence" is an alternative form of SC2H. Alleles result from a mutation, ie, a change in the nucleic acid sequence, and generally produce altered mRNAs or polypeptides whose structure or function may or may not be altered. Any given gene may have none, one or many allelic forms. Common mutational changes which give rise to alleles are generally ascribed to natural deletions, additions or substitutions of amino acids. Each of these types of changes may occur alone, or in combination with the others, one or more times in a given sequence.

Methods for DNA sequencing are well known in the art and employ such enzymes as the Klenow fragment of DNA polymerase I, SEQUENASE® (US Biochemical Corp, Cleveland Ohio), Taq polymerase (Perkin Elmer, Norwalk Conn.), thermostable T7 polymerase (Amersham, Chicago Ill.), or combinations of recombinant polymerases and proofreading exonucleases such as the ELONGASE Amplification System marketed by Gibco BRL (Gaithersburg Md.). Preferably, the process is automated with machines such as the Hamilton Micro Lab 2200 (Hamilton, Reno Nev.), Peltier Thermal Cycler (PTC200; MJ Research, Watertown Mass.) and the ABI 377 DNA sequencers (Perkin Elmer).

EXTENDING THE POLYNUCLEOTIDE SEQUENCE

The polynucleotide sequence encoding SC2H may be extended utilizing partial nucleotide sequence and various methods known in the art to detect upstream sequences such as promoters and regulatory elements. Gobinda et al (1993; PCR Methods Applic 2:318–22) disclose "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T et al (1988) Nucleic Acids Res 16:8186). The primers may be designed using OLIGO® 4.06 Primer Analysis Software (1992; National Biosciences Inc, Plymouth Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M et al (1991) PCR Methods Applic 1:111–19) is a method for PCR amplification of DNA fragments adjacent to a known sequence in human and yeast artificial chromosome DNA. Capture PCR also requires multiple restriction enzyme digestions and ligations to place an engineered double-stranded sequence into an unknown portion of the DNA molecule before PCR.

Another method which may be used to retrieve unknown sequences is that of Parker JD et al (1991; Nucleic Acids Res 19:3055–60). Additionally, one can use PCR, nested primers and PromoterFinder libraries to walk in genomic DNA (PROMOTERFINDER™ Clontech (Palo Alto, Calif.). This process avoids the need to screen libraries and is useful in finding intron/exon junctions.

Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension into the 5' nontranslated regulatory region.

Capillary electrophoresis may be used to analyze the size or confirm the nucleotide sequence of sequencing or PCR products. Systems for rapid sequencing are available from Perkin Elmer, Beckman Instruments (Fullerton Calif.), and other companies. Capillary sequencing may employ flowable polymers for electrophoretic separation, four different fluorescent dyes (one for each nucleotide) which are laser activated, and detection of the emitted wavelengths by a charge coupled device camera. Output/light intensity is converted to electrical signal using appropriate software (eg. GENOTYPER™ and SEQUENCE NAVIGATOR™ from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez MC et al (1993) Anal Chem 65:2851–8).

EXPRESSION OF THE NUCLEOTIDE SEQUENCE

In accordance with the present invention, polynucleotide sequences which encode SC2H, fragments of the polypeptide, fusion proteins or functional equivalents thereof may be used in recombinant DNA molecules that direct the expression of SC2H in appropriate host cells. Due to the inherent degeneracy of the genetic code, other DNA sequences which encode substantially the same or a functionally equivalent amino acid sequence, may be used to clone and express SC2H. As will be understood by those of skill in the art, it may be advantageous to produce SC2H-encoding nucleotide sequences possessing non-naturally occurring codons. Codons preferred by a particular prokaryotic or eukaryotic host (Murray E et al (1989) Nuc Acids Res 17:477–508) can be selected, for example, to increase the rate of SC2H expression or to produce recombinant RNA transcripts having desirable properties, such as a longer half-life, than transcripts produced from naturally occurring sequence.

The nucleotide sequences of the present invention can be engineered in order to alter a coding sequence of SC2H for a variety of reasons, including but not limited to, alterations which modify the cloning, processing and/or expression of the gene product. For example, mutations may be introduced using techniques which are well known in the art, eg, site-directed mutagenesis to insert new restriction sites, to alter glycosylation patterns, to change codon preference, to produce splice variants, etc.

In another embodiment of the invention, a natural, modified or recombinant nucleotide sequence encoding SC2H may be ligated to a heterologous sequence to encode a fusion protein. For example, for screening of peptide libraries for inhibitors of SC2H activity, it may be useful to encode a chimeric SC2H protein that is recognized by a commercially available antibody. A fusion protein may also be engineered to contain a cleavage site located between an SC2H sequence and the heterologous protein sequence, so that the SC2H may be cleaved and substantially purified away from the heterologous moiety.

In an alternate embodiment of the invention, the coding sequence for SC2H may be synthesized, whole or in part, using chemical methods well known in the art (see Caruthers MH et al (1980) Nuc Acids Res Symp Ser 215–23, Horn T et al(1980) Nuc Acids Res Symp Ser 225–32, etc). Alternatively, the protein itself could be produced using chemical methods to synthesize an SC2H amino acid sequence, whole or in part. For example, peptide synthesis can be performed using various solid-phase techniques (Roberge JY et al (1995) Science 269:202–204) and automated synthesis may be achieved, for example, using the ABI 431A Peptide Synthesizer (Perkin Elmer) in accordance with the instructions provided by the manufacturer.

The newly synthesized peptide can be substantially purified by preparative high performance liquid chromatography (eg, Creighton (1983) *Proteins, Structures and Molecular Principles*, WH Freeman and Co, New York N.Y.). The composition of the synthetic peptides may be confirmed by amino acid analysis or sequencing (eg, the Edman degradation procedure; Creighton, supra). Additionally the amino acid sequence of SC2H, or any part thereof, may be altered during direct synthesis and/or combined using chemical methods with sequences from other proteins, or any part thereof, to produce a variant polypeptide.

EXPRESSION SYSTEMS

In order to express a biologically active SC2H, the nucleotide sequence encoding SC2H or its functional equivalent, is inserted into an appropriate expression vector, ie, a vector which contains the necessary elements for the transcription and translation of the inserted coding sequence.

Methods which are well known to those skilled in the art can be used to construct expression vectors containing an SC2H coding sequence and appropriate transcriptional or translational controls. These methods include in vitro recombinant DNA techniques, synthetic techniques and in vivo recombination or genetic recombination. Such techniques are described in Sambrook et al (1989) *Molecular Cloning, A Laboratory Manual*, Cold Spring Harbor Press, Plainview N.Y. and Ausubel FM et al (1989) *Current Protocols in Molecular Biology*, John Wiley & Sons, New York N.Y.

A variety of expression vector/host systems may be utilized to contain and express an SC2H coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (eg, baculovirus); plant cell systems transfected with virus expression vectors (eg, cauliflower mosaic virus, CaMV; tobacco mosaic virus, TMV) or transformed with bacterial expression vectors (eg, Ti or pBR322 plasmid); or animal cell systems.

The "control elements" or "regulatory sequences" of these systems vary in their strength and specificities and are those nontranslated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT® phagemid (Stratagene, LaJolla, Calif.) or pSport1 (Gibco BRL) and ptrp-lac hybrids and the like may be used. The baculovirus polyhedrin promoter may be used in insect cells. Promoters or enhancers derived from the genomes of plant cells (eg, heat shock, RuBisCo; and storage protein genes) or from plant viruses (eg, viral promoters or leader sequences) may be cloned into the vector. In mammalian cell systems, promoters from the mammalian genes or from mammalian viruses are most appropriate. If it is necessary to generate a cell line that contains multiple copies of SC2H, vectors based on SV40 or EBV may be used with an appropriate selectable marker.

In bacterial systems, a number of expression vectors may be selected depending upon the use intended for SC2H. For example, when large quantities of SC2H are needed for the induction of antibodies, vectors which direct high level expression of fusion proteins that are readily purified may be desirable. Such vectors include, but are not limited to, the multifunctional *E. coli* cloning and expression vectors such as BLUESCRIPT® (Stratagene), in which the SC2H coding sequence may be ligated into the vector in frame with sequences for the amino-terminal Met and the subsequent 7 residues of β-galactosidase so that a hybrid protein is produced; pIN vectors (Van Heeke & Schuster (1989) J Biol Chem 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase and PGH may be used. For reviews, see Ausubel et al (supra) and Grant et al (1987) Methods in Enzymology 153:516–544.

In cases where plant expression vectors are used, the expression of a sequence encoding SC2H may be driven by any of a number of promoters. For example, viral promoters such as the 35S and 19S promoters of CaMV (Brisson et al (1984) Nature 310:511–514) may be used alone or in combination with the omega leader sequence from TMV (Takamatsu et al (1987) EMBO J 6:307–311). Alternatively, plant promoters such as the small subunit of RuBisCo (Coruzzi et al (1984) EMBO J 3:1671–1680; Broglie et al (1984) Science 224:838–843); or heat shock promoters (Winter J and Sinibaldi RM (1991) Results Probl Cell Differ 17:85–105) may be used. These constructs can be introduced into plant cells by direct DNA transformation or pathogen-mediated transfection. For reviews of such techniques, see Hobbs S or Murry LE in McGraw Hill *Yearbook of Science and Technology* (1992) McGraw Hill New York N.Y., pp 191–196 or Weissbach and Weissbach (1988) *Methods for Plant Molecular Biology*, Academic Press, New York N.Y., pp 421–463.

An alternative expression system which could be used to express SC2H is an insect system. In one such system, *Autographa californica* nuclear polyhedrosis virus (AcNPV) is used as a vector to express foreign genes in *Spodootera fruaiperda* cells or in Trichoolusia larvae. The SC2H coding sequence may be cloned into a nonessential region of the virus, such as the polyhedrin gene, and placed under control of the polyhedrin promoter. Successful insertion of the SC2H coding sequence will render the polyhedrin gene inactive and produce recombinant virus lacking coat protein. The recombinant viruses are then used to infect *S. frugiperda* cells or Trichonlusia larvae in which SC2H is expressed (Smith et al (1983) J Virol 46:584; Engelhard EK et al (1994) Proc Nat Acad Sci 91:3224–7).

In mammalian host cells, a number of viral-based expression systems may be utilized. In cases where an adenovirus is used as an expression vector, a coding sequence for SC2H may be ligated into an adenovirus transcription/translation complex consisting of the late promoter and tripartite leader sequence. Insertion in a nonessential E1 or E3 region of the viral genome will result in a viable virus capable of expressing SC2H in infected host cells (Logan and Shenk (1984) Proc Natl Acad Sci 81:3655–59). In addition, transcription enhancers, such as the rous sarcoma virus (RSV) enhancer, may be used to increase expression in mammalian host cells.

Specific initiation signals may also be required for efficient translation of an SC2H sequence. These signals include the ATG initiation codon and adjacent sequences. In cases where nucleic acid encoding SC2H, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D et al (1994) Results Probl Cell Differ 20:125–62; Bittner et al (1987) Methods in Enzymol 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express SC2H may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M et al (1977) Cell 11:223–32) and adenine phosphoribosyltransferase (Lowy I et al (1980) Cell 22:817–23) genes which can be employed in tk- or aprt- cells, respectively. Also, antimetabolite, antibiotic or herbicide resistance can be used as the basis for selection; for example, dhfr which confers resistance to methotrexate (Wigler M et al (1980) Proc Natl Acad Sci 77:3567–70); npt, which confers resistance to the aminoglycosides neomycin and G-418 (Colbere-Garapin F et al (1981) J Mol Biol 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman SC and RC Mulligan (1988) Proc Natl Acad Sci 85:8047–51). Recently, the use of visible markers has gained popularity with such markers as anthocyanins, β glucuronidase and its substrate, GUS, and luciferase and its substrate, luciferin, being widely used not only to identify transformants, but also to quantify the amount of transient or stable protein expression attributable to a specific vector system (Rhodes Calif. et al (1995) Methods Mol Biol 55:121–131).

IDENTIFICATION OF TRANSFORMANTS CONTAINING THE POLYNUCLEOTIDE SEQUENCE

Although the presence/absence of marker gene expression suggests that the gene of interest is also present, its presence and expression should be confirmed. For example, if the SC2H polynucleotide sequence is inserted within a marker gene sequence, recombinant cells containing SC2H can be identified by the absence of marker gene function. Alternatively, a marker gene can be placed in tandem with an SC2H sequence under the control of a single promoter. Expression of the marker gene in response to induction or selection usually indicates expression of the tandem SC2H as well.

Alternatively, host cells which contain the coding sequence for SC2H and express SC2H may be identified by a variety of procedures known to those of skill in the art. These procedures include, but are not limited to, DNA-DNA or DNA-RNA hybridization and protein bioassay or immunoassay techniques which include membrane, solution, or chip based technologies for the detection and/or quantification of the nucleic acid or protein.

The presence of the polynucleotide sequence encoding SC2H can be detected by DNA-DNA or DNA-RNA hybridization or amplification using probes, portions or fragments of SC2H-encoding nucleotides. Nucleic acid amplification based assays involve the use of oligonucleotides or oligomers based on the SC2H sequence to detect transformants containing SC2H DNA or RNA. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer.

A variety of protocols for detecting and measuring the expression of SC2H, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on SC2H is preferred, but a competitive binding assay may be employed. These and other assays are described, among other places, in Hampton R et al (1990*, Serological Methods, a Laboratory Manual*, APS Press, St Paul Minn.) and Maddox DE et al (1983, J Exp Med 158:1211).

A wide variety of labels and conjugation techniques are known by those skilled in the art and can be used in various nucleic acid and amino acid assays. Means for producing labeled hybridization or PCR probes for detecting sequences related to SC2H include oligolabeling, nick translation, end-labeling or PCR amplification using a labeled nucleotide. Alternatively, the SC2H sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway, N.J.), Promega (Madison, Wis.), and US Biochemical Corp (Cleveland, Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced as shown in U.S. Pat. No. 4,816,567 incorporated herein by reference.

PURIFICATION OF SC2H

Host cells transformed with an SC2H-encoding nucleotide sequence may be cultured under conditions suitable for the expression and recovery of the encoded protein from cell culture. The protein produced by a recombinant cell may be contained intracellularly or secreted depending on the sequence and/or the vector used. As will be understood by those of skill in the art, expression vectors containing SC2H can be designed for efficient production and proper transmembrane insertion of SC2H into a prokaryotic or eukaryotic cell membrane. Other recombinant constructions may join SC2H to nucleotide sequence encoding a polypeptide domain which will facilitate purification of soluble proteins (Kroll DJ et al (1993) DNA Cell Biol 12:441–53; cf discussion of vectors infra containing fusion proteins).

SC2H may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle, Wash.). The inclusion of a cleavable linker sequences such as Factor XA or enterokinase (Invitrogen, San Diego, Calif.) between the purification domain and SC2H is useful to facilitate purification. One such expression vector provides for expression of a fusion protein compromising an SC2H and contains nucleic acid encoding 6 histidine residues followed by thioredoxin and an enterokinase cleavage site. The histidine residues facilitate purification on IMIAC (immobilized metal ion affinity chromatography as described in Porath et al (1992) Protein Expression and Purification 3: 263–281) while the enterokinase cleavage site provides a means for purifying the glycoprotein from the fusion protein.

In addition to recombinant production, fragments of SC2H may be produced by direct peptide synthesis using solid-phase techniques (cf Stewart et al (1969) *Solid-Phase Peptide Synthesis*, WH Freeman Co, San Francisco; Merrifield J (1963) J Am Chem Soc 85:2149–2154). In vitro protein synthesis may be performed using manual techniques or by automation. Automated synthesis may be achieved, for example, using Applied Biosystems 431A Peptide Synthesizer (Perkin Elmer, Foster City Calif.) in accordance with the instructions provided by the manufacturer. Various fragments of SC2H may be chemically synthesized separately and combined using chemical methods to produce the full length molecule.

USES OF SC2H

The rationale for the use of polynucleotide and polypeptide sequences disclosed herein is based in part on the structural homology among the novel SC2H and rat and yeast SC2 glycoproteins.

Synapse formation or maintenance facilitated by SC2H may influence synaptic density and affect the release of neurotransmitters or the propagation of nerve impulses. Therefore, a diagnostic test for altered expression of SC2H can accelerate diagnosis and proper treatment of conditions caused by altered or decreased synaptic contacts or impaired neurotransmitter release, such as Alzheimer disease, neuromuscular conditions such as Parkinson disease, Huntington disease, ALS, or other physiological or pathological problems associated with abnormal neuronal function.

Viral pathogens attach to host cell surfaces by the interaction of viral envelope glycoproteins with host membrane glycoproteins. This viral attachment is the first step in the infective cycle for numerous pathogens, including those which attack the nervous system such as poliovirus, rabies, herpes simplex, and HIV. Invasion of viral pathogens may be controlled by preventing the interaction of viral envelope glycoproteins with host-cell SC2H glycoprotein.

SC2H or its soluble extracellular domain can be used to identify specific cell surface or viral envelope glycoproteins with which SC2H interacts. The extracellular domain of SC2H may be used as an inhibitor of virus-host cell attachment by binding to the viral envelope glycoproteins and thus blocking virus attachment to host membrane SC2H. Alternatively, antibodies raised against the extracellular domain of SC2H may inhibit interaction of the viral protein with SC2H, thereby blocking virus-host attachment.

In some instances, for instance overexpression associated with disorders such as Alzheimer disease, it may be advantageous to suppress SC2H expression. SC2H expression could be suppressed by administration of SC2H antisense oligonucleotides. Alternatively, specific antibodies against SC2H may be introduced to treat diseases or conditions associated with abnormal SC2H expression.

SC2H ANTIBODIES

SC2H-specific antibodies are useful for the diagnosis of conditions and diseases associated with expression of SC2H. Such antibodies may include, but are not limited to, polyclonal, monoclonal, chimeric, single chain, Fab fragments and fragments produced by a Fab expression library. Neutralizing antibodies, ie, those which inhibit dimer formation, are especially preferred for diagnostics and therapeutics.

SC2H for antibody induction does not require biological activity; however, the protein fragment, or oligopeptide must be antigenic. Peptides used to induce specific antibodies may have an amino acid sequence consisting of at least five amino acids, preferably at least 10 amino acids. Preferably, they should mimic a portion of the amino acid sequence of the natural protein and may contain the entire amino acid sequence of a small, naturally occurring molecule. Short stretches of SC2H amino acids may be fused with those of another protein such as keyhole limpet hemocyanin and antibody produced against the chimeric molecule. Procedures well known in the art can be used for the production of antibodies to SC2H.

For the production of antibodies, various hosts including goats, rabbits, rats, mice, etc may be immunized by injection with SC2H or any portion, fragment or oligopeptide which retains immunogenic properties. Depending on the host species, various adjuvants may be used to increase immunological response. Such adjuvants include but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Monoclonal antibodies to SC2H may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) *Monoclonal Antibodies and Cancer Therapy*, Alan R Liss Inc, New York N.Y., pp 77–96).

In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,778) can be adapted to produce SC2H-specific single chain antibodies Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G and Milstein C (1991; Nature 349:293–299).

Antibody fragments which contain specific binding sites for SC2H may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse WD et al (1989) Science 256:1275–1281).

A variety of protocols for competitive binding or immunoradiometric assays using either polyclonal or monoclonal antibodies with established specificities are well known in the art. Such immunoassays typically involve the formation of complexes between SC2H and its specific antibody and the measurement of complex formation. A two-site, monoclonal-based immunoassay utilizing monoclonal antibodies reactive to two noninterfering epitopes on a specific SC2H protein is preferred, but a competitive binding assay may also be employed. These assays are described in Maddox DE et al (1983, J Exp Med 158:1211).

DIAGNOSTIC ASSAYS USING SC2H SPECIFIC ANTIBODIES

Particular SC2H antibodies are useful for the diagnosis of conditions or diseases characterized by expression of SC2H or in assays to monitor patients being treated with SC2H, agonists or inhibitors. Diagnostic assays for SC2H include methods utilizing the antibody and a label to detect SC2H in human body fluids or extracts of cells or tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring SC2H, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on SC2H is preferred, but a competitive binding assay may be employed. These assays are described, among other places, in Maddox, DE et al (1983, J Exp Med 158:1211).

In order to provide a basis for diagnosis, normal or standard values for SC2H expression must be established. This is accomplished by combining body fluids or cell extracts taken from normal subjects, either animal or human, with antibody to SC2H under conditions suitable for complex formation which are well known in the art. The amount of standard complex formation may be quantified by comparing various artificial membranes containing known quantities of SC2H with both control and disease samples from biopsied tissues. Then, standard values obtained from normal samples may be compared with values obtained from samples from subjects potentially affected by disease. Deviation between standard and subject values establishes the presence of disease state.

DRUG SCREENING

SC2H, its catalytic or immunogenic fragments or oligopeptides thereof, can be used for screening therapeutic compounds in any of a variety of drug screening techniques. The fragment employed in such a test may be free in solution, affixed to a solid support, borne on a cell surface, or located intracellularly. The formation of binding complexes, between SC2H and the agent being tested, may be measured.

Another technique for drug screening which may be used for high throughput screening of compounds having suitable binding affinity to the SC2H is described in detail in "Determination of Amino Acid Sequence Antigenicity" by Geysen HN, WO Application 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of SC2H and washed. Bound SC2H is then detected by methods well known in the art. Substantially purified SC2H can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding SC2H specifically compete with a test compound for binding SC2H. In this manner, the antibodies can be used to detect the presence of any peptide which shares one or more antigenic determinants with SC2H.

USES OF THE POLYNUCLEOTIDE ENCODING SC2H

A polynucleotide encoding SC2H, or any part thereof, may be used for diagnostic and/or therapeutic purposes. For diagnostic purposes, the SC2H of this invention may be used to detect and quantitate gene expression in biopsied tissues in which expression of SC2H may be implicated. The diagnostic assay is useful to distinguish between absence, presence, and excess expression of SC2H and to monitor regulation of SC2H levels during therapeutic intervention. Included in the scope of the invention are oligonucleotide sequences, antisense RNA and DNA molecules, and PNAs.

Another aspect of the subject invention is to provide for hybridization or PCR probes which are capable of detecting polynucleotide sequences, including genomic sequences, encoding SC2H or closely related molecules. The specificity of the probe, whether it is made from a highly specific region, eg, 10 unique nucleotides in the 5' regulatory region, or a less specific region, eg, especially in the 3' region, and the stringency of the hybridization or amplification (maximal, high, intermediate or low) will determine whether the probe identifies only naturally occurring SC2H, alleles or related sequences.

Probes may also be used for the detection of related sequences and should preferably contain at least 50% of the nucleotides from any of these SC2H encoding sequences. The hybridization probes of the subject invention may be derived from the nucleotide sequence of SEQ ID NO:2 or from genomic sequence including promoter, enhancer elements and introns of the naturally occurring SC2H. Hybridization probes may be labeled by a variety of reporter groups, including radionuclides such as $^{32}P$ or $^{35}S$, or enzymatic labels such as alkaline phosphatase coupled to the probe via avidin/biotin coupling systems, and the like.

Other means for producing specific hybridization probes for SC2H DNAs include the cloning of nucleic acid sequences encoding SC2H or SC2H derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

Diagnostics

Polynucleotide sequences encoding SC2H may be used for the diagnosis of conditions or diseases with which the expression of SC2H is associated. For example, polynucleotide sequences encoding SC2H may be used in hybridization or PCR assays of fluids or tissues from biopsies to detect SC2H expression. The form of such qualitative or quantitative methods may include Southern or northern analysis, dot blot or other membrane-based technologies; PCR technologies; dip stick, pin, chip and ELISA technologies. All of these techniques are well known in the art and are the basis of many commercially available diagnostic kits.

The SC2H nucleotide sequence disclosed herein provide the basis for assays that detect activation or induction associated with inflammation or disease. The SC2H nucleotide sequence may be labeled by methods known in the art and added to a fluid or tissue sample from a patient under conditions suitable for the formation of hybridization complexes. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye in the biopsied or extracted sample is significantly elevated over that of a comparable control sample, the nucleotide sequence has hybridized with nucleotide sequences in the sample, and the presence of elevated levels of SC2H nucleotide sequences in the sample indicates the presence of the associated inflammation and/or disease.

Such assays may also be used to evaluate the efficacy of a particular therapeutic treatment regime in animal studies, in clinical trials, or in monitoring the treatment of an individual patient. In order to provide a basis for the diagnosis of disease, a normal or standard profile for SC2H expression must be established. This is accomplished by combining body fluids or cell extracts taken from normal subjects, either animal or human, with SC2H, or a portion thereof, under conditions suitable for hybridization or amplification. Standard hybridization may be quantified by comparing the values obtained for normal subjects with a dilution series of SC2H run in the same experiment where a known amount of substantially purified SC2H is used. Standard values obtained from normal samples may be compared with values obtained from samples from patients afflicted with SC2H-associated diseases. Deviation between standard and subject values is used to establish the presence of disease.

Once disease is established, a therapeutic agent is administered and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

Polymerase Chain Reaction (PCR) as described in U.S. Pat. Nos. 4,683,195 and 4,965,188 provides additional uses for oligonucleotides based upon the SC2H sequence. Such oligomers are generally chemically synthesized, but they may be generated enzymatically or produced from a recombinant source. Oligomers generally comprise two nucleotide sequences, one with sense orientation (5'→3') and one with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally, methods which may be used to quantitate the expression of a particular molecule include radiolabeling (Melby PC et al 1993 J Immunol Methods 159:235–44) or biotinylating (Duplaa C et al 1993 Anal Biochem 229–36) nucleotides, coamplification of a control nucleic acid, and standard curves onto which the experimental results are interpolated. Quantitation of multiple samples may be speeded up by running the assay in an ELISA format where the oligomer of interest is presented in various dilutions and a spectrophotometric or colorimetric response gives rapid quantitation. A definitive diagnosis of this type may allow health professionals to begin aggressive treatment and prevent further worsening of the condition. Similarly, further assays can be used to monitor the progress of a patient during treatment. Furthermore, the nucleotide sequences disclosed herein may be used in molecular biology techniques that have not yet been developed, provided the new techniques rely on properties of nucleotide sequences that are currently known such as the triplet genetic code, specific base pair interactions, and the like.

Therapeutic Use

Based upon its homology to the gene encoding rat SC2 and its expression profile, the SC2H polynucleotide disclosed herein may provide the basis for the design of molecules for the treatment of diseases such as Alzheimer disease, Huntington disease, Parkinson disease and ALS and for the prevention of invasion by viral pathogens such as HIV, rabies, and poliovirus.

Expression vectors derived from retroviruses, adenovirus, herpes or vaccinia viruses, or from various bacterial plasmids, may be used for delivery of nucleotide sequences to the targeted organ, tissue or cell population. Methods which are well known to those skilled in the art can be used to construct recombinant vectors which will express antisense SC2H. See, for example, the techniques described in Sambrook et al (supra) and Ausubel et al (supra).

The polynucleotides comprising full length cDNA sequence and/or its regulatory elements enable researchers to use SC2H as an investigative tool in sense (Youssoufian H and HF Lodish 1993 Mol Cell Biol 13:98–104) or antisense (Eguchi et al (1991) Annu Rev Biochem 60:631–652) regulation of gene function. Such technology is now well known in the art, and sense or antisense oligomers, or larger fragments, can be designed from various locations along the coding or control regions.

Genes encoding SC2H can be turned off by transfecting a cell or tissue with expression vectors which express high levels of a desired SC2H fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector (Mettler I, personal communication) and even longer if appropriate replication elements are part of the vector system.

As mentioned above, modifications of gene expression can be obtained by designing antisense molecules, DNA, RNA or PNA, to the control regions of SC2H, ie, the promoters, enhancers, and introns. Oligonucleotides derived from the transcription initiation site, eg, between −10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee JE et al (In: Huber BE and BI Carr (1994) *Molecular and Immunologic Approaches*, Futura Publishing Co, Mt Kisco N.Y.).

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of RNA encoding SC2H.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding SC2H. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex vivo therapy. For ex vivo therapy, vectors are introduced into stem cells taken from the patient and clonally propagated for autologous transplant back into that same patient as presented in U.S. Pat. Nos. 5,399,493 and 5,437,994, disclosed herein by reference. Delivery by transfection and by liposome are quite well known in the art.

Furthermore, the nucleotide sequences for SC2H disclosed herein may be used in molecular biology techniques that have not yet been developed, provided the new techniques rely on properties of nucleotide sequences that are currently known, including but not limited to such properties as the triplet genetic code and specific base pair interactions.

DETECTION AND MAPPING OF RELATED POLYNUCLEOTIDE SEQUENCES

The nucleic acid sequence for SC2H can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price CM (1993; Blood Rev 7:127–34) and Trask BJ (1991; Trends Genet 7:149–54).

The technique of fluorescent in situ hybridization of chromosome spreads has been described, among other places, in Verma et al (1988) *Human Chromosomes: A Manual of Basic Techniques*, Pergamon Press, New York N.Y. Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of an SC2H on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

In situ hybridization of chromosomal preparations and physical mapping techniques such as linkage analysis using established chromosomal markers may be used for extending genetic maps. For example, an STS based map of the human genome was recently published by the Whitehead-MIT Center for Genomic Research (Hudson TJ et al (1995) Science 270:1945–1954). Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22-23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier or affected individuals.

PHARMACEUTICAL COMPOSITIONS

The present invention relates to pharmaceutical compositions which may comprise nucleotides, proteins, antibodies, agonists, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

Administration of Pharmaceutical Compositions

Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Manufacture and Storage

The pharmaceutical compositions of the present invention may be manufactured in a manner that is known in the art, eg, by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%–2% sucrose, 2%–7% mannitol at a pH range of 4.5 to 5.5 that is combined with buffer prior to use.

After pharmaceutical compositions comprising a compound of the invention formulated in an acceptable carrier have been prepared, they can be placed in an appropriate container and labeled for treatment of an indicated condition. For administration of SC2H, such labeling would include amount, frequency and method of administration.

Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, eg, of neoplastic cells, or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, eg, ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg, tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for nucleotides than for proteins or their inhibitors. Similarly, delivery of polynucleotides or polypeptides will be specific to particular cells, conditions, locations, etc.

The examples below are provided to illustrate the subject invention and are not included for the purpose of limiting the invention.

EXAMPLES

I cDNA Library Construction

The BRAINOT03 cDNA library was constructed from normal brain tissue removed from a 26 year old male. The frozen tissue was homogenized and lysed using a Brinkmann Homogenizer Polytron PT-3000 (Brinkmann Instruments, Westbury N.J.). The reagents and extraction procedures were used as supplied in the Stratagene RNA Isolation Kit (Cat. #200345; Stratagene). The lysate was centrifuged over a 5.7M CsCl cushion using an Beckman SW28 rotor in a Beckman L8-70M Ultracentrifuge (Beckman Instruments) for 18 hours at 25,000 rpm at ambient temperature. The RNA was extracted once with phenol chloroform pH 8.0, once with acid phenol pH 4.0, precipitated using 0.3M sodium acetate and 2.5 volumes of ethanol, resuspended in water and DNase treated for 15 min at 37° C. The RNA was isolated using the Qiagen Oligotex kit (QIAGEN Inc, Chatsworth Calif.) and used to construct the cDNA library.

The RNA was handled according to the recommended protocols in the SuperScript Plasmid System for cDNA Synthesis and Plasmid Cloning (Cat. #18248-013; Gibco/BRL). cDNAs were fractionated on a Sepharose CL4B column (Cat. #275105, Pharmacia), and those cDNAs exceeding 400 bp were ligated into pSport I. The plasmid pSport I was subsequently transformed into DH5a™ competent cells (Cat. #18258-012, Gibco/BRL).

II Isolation and Sequencing of cDNA Clones

Plasmid DNA was released from the cells and purified using the Miniprep Kit (Cat. #77468; Advanced Genetic Technologies Corporation, Gaithersburg Md.). This kit consists of a 96 well block with reagents for 960 purifications. The recommended protocol was employed except for the following changes: 1) the 96 wells were each filled with only 1 ml of sterile Terrific Broth (Cat. #22711, LIFE TECHNOLOGIES™, Gaithersburg Md.) with carbenicillin at 25 mg/L and glycerol at 0.4%; 2) the bacteria were cultured for 24 hours after the wells were inoculated and then lysed with 60 $\mu$l of lysis buffer; 3) a centrifugation step employing the Beckman GS-6R @2900 rpm for 5 min was performed before the contents of the block were added to the primary filter plate; and 4) the optional step of adding isopropanol to TRIS buffer was not routinely performed. After the last step in the protocol, samples were transferred to a Beckman 96-well block for storage.

The cDNAs were sequenced by the method of Sanger F and AR Coulson (1975; J Mol Biol 94:441f), using a Hamilton Micro Lab 2200 (Hamilton, Reno Nev.) in combination with four Peltier Thermal Cyclers (PTC200; MJ Research, Watertown Mass.) and Applied Biosystems 377 DNA Sequencing Systems (Perkin Elmer), and reading frame was determined.

III Homology Searching of cDNA Clones and Their Deduced Proteins

Each cDNA was compared to sequences in GenBank using a search algorithm developed by Applied Biosystems and incorporated into the INHERIT™ 670 Sequence Analysis System. In this algorithm, Pattern Specification Language (TRW Inc, Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul SF (1993) J Mol Evol 36:290–300; Altschul, SF et al (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al. supra).

Analogous computer techniques use BLAST (Altschul SF 1993 and 1990, supra) to search for identical or related molecules in nucleotide databases such as GenBank or the LIFESEQ™ database (Incyte, Palo Alto Calif.). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

and it takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

V Extension of SC2H to Full Length or to Recover Regulatory Elements

The nucleic acid sequence encoding full length SC2H (SEQ ID NO:2) is used to design oligonucleotide primers for extending a partial nucleotide sequence to full length or for obtaining 5' sequences from genomic libraries. One primer is synthesized to initiate extension in the antisense direction (XLR) and the other is synthesized to extend sequence in the sense direction (XLF). Primers allow the extension of the known SC2H nucleotide sequence "outward" generating amplicons containing new, unknown nucleotide sequence for the region of interest (U.S. patent application Ser. No. 08/487,112, filed Jun. 7, 1995, now abandoned specifically incorporated by reference). The initial primers are designed from the cDNA using OLIGO® 4.06 Primer Analysis Software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; MJ Research, Watertown Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture is analyzed by electrophoresis on a low concentration (about 0.6–0.8%) agarose mini-gel to determine which reactions were successful in extending the sequence. Bands thought to contain the largest products were selected and cut out of the gel. Further purification involves using a commercial gel extraction method such as QIAQuick™ (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 µl of ligation buffer, 1 µl T4-DNA ligase (15 units) and 1 µl T4 polynucleotide kinase are added, and the mixture is incubated at room temperature for 2–3 hours or overnight at 16° C. Competent *E. coli* cells (in 40 µl of appropriate media) are transformed with 3 µl of ligation mixture and cultured in 80 µl of SOC medium (Sambrook J et al, supra). After incubation for one hour at 37° C., the whole transformation mixture is plated on Luria Bertani (LB)-agar (Sambrook J et al, supra) containing 2× Carb. The following day, several colonies are randomly picked from each plate and cultured in 150 µl of liquid LB/2× Carb medium placed in an individual well of an appropriate, commercially-available, sterile 96-well microtiter plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3×) containing 4 units of rTth DNA polymerase, a vector primer and one or both of the gene specific primers used for the extension reaction are added to each well. Amplification is performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 40° C. (and holding) |

Aliquots of the PCR reactions are run on agarose gels together with molecular weight markers. The sizes of the PCR products are compared to the original partial cDNAs, and appropriate clones are selected, ligated into plasmid and sequenced.

VI Labeling and Use of Hybridization Probes

Hybridization probes derived from SEQ ID NO:2 are employed to screen cDNAs, genomic DNAs or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 mCi of [$\gamma$-$^{32}$P] adenosine triphosphate (Amersham, Chicago Ill.) and T4 polynucleotide kinase (DuPont NEN®, Boston Mass.). The labeled oligonucleotides are substantially purified with Sephadex G-25 super fine resin column (Pharmacia). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under increasingly stringent conditions up to 0.1 x saline sodium citrate and 0.5% sodium dodecyl sulfate. After XOMAT AR™ film (Kodak, Rochester N.Y.) is exposed to the blots in a Phosphoimager cassette (Molecular Dynamics, Sunnyvale Calif.) for several hours, hybridization patterns are compared visually.

VII Antisense Molecules

The nucleotide sequence encoding SC2H, or any part thereof, is used to inhibit in vivo or in vitro expression of naturally occurring SC2H. Although use of antisense oligonucleotides, comprising about 20 base-pairs, is specifically described, essentially the same procedure is used with larger cDNA fragments. An oligonucleotide based on the coding sequence of SC2H as shown in FIGS. 1A, 1B, and 1C is used to inhibit expression of naturally occurring SC2H. The complementary oligonucleotide is designed from the most unique 5' sequence as shown in FIGS. 1A, 1B, and 1C and used either to inhibit transcription by preventing promoter binding to the upstream nontranslated sequence or translation of an SC2H transcript by preventing the ribosome from binding. Using an appropriate portion of the leader and 5' sequence of SEQ ID NO:2, an effective antisense oligonucleotide includes any 15–20 nucleotides spanning the region which translates into the signal or early coding sequence of the polypeptide as shown in FIGS. 1A, 1B, and 1C.

VIII Expression of SC2H

Expression of the extracellular domain of SC2H is accomplished by subcloning the cDNAs into appropriate vectors and transfecting the vectors into host cells. In this case, the cloning vector, pSport, previously used for the generation of the cDNA library is used to express SC2H in *E. coli*. Upstream of the cloning site, this vector contains a promoter for β-galactosidase, followed by sequence containing the amino-terminal Met and the subsequent 7 residues of β-galactosidase. Immediately following these eight residues is a bacteriophage promoter useful for transcription and a linker containing a number of unique restriction sites.

Induction of an isolated, transfected bacterial strain with IPTG using standard methods produces a fusion protein which consists of the first seven residues of β-galactosidase, about 5 to 15 residues of linker, and the full length SC2H. The signal sequence directs the secretion of the extracellular domain of SC2H into the bacterial growth media which can be used directly in the following assay for activity.

IX SC2H Activity

The binding activity of SC2H or biologically active fragments thereof may be assayed by first labeling the SC2H protein or polypeptide with $^{125}$I Bolton-Hunter reagent (Bolton, AE and Hunter, WM (1973) Biochem J 133:529). Candidate ligands (including glycoproteins, virus particles or whole cells) previously arrayed in the wells of a 96 well plate are incubated with the labeled SC2H, washed and any wells with labeled SC2H complex are assayed by radioactivity quantitation. Data obtained using different concentrations of SC2H are used to calculate values for the number, affinity, and association of SC2H with the candidate ligands.

X Production of SC2H Specific Antibodies

SC2H substantially purified using PAGE electrophoresis (Sambrook, supra) is used to immunize rabbits and to produce antibodies using standard protocols. The amino acid sequence translated from SC2H is analyzed using DNAStar software (DNAStar Inc) to determine regions of high immunogenicity and a corresponding oligopolypeptide is synthesized and used to raise antibodies by means known to those of skill in the art. Analysis to select appropriate epitopes, such as those near the C-terminus or in hydrophilic regions (shown in FIG. 3) is described by Ausubel FM et al (supra).

Typically, the oligopeptides are 15 residues in length, synthesized using an Applied Biosystems Peptide Synthesizer Model 431A using fmoc-chemistry, and coupled to keyhole limpet hemocyanin (KLH, Sigma) by reaction with M-maleimidobenzoyl-N-hydroxysuccinimide ester (MBS; Ausubel FM et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring SC2H Using Specific Antibodies

Naturally occurring or recombinant SC2w is substantially purified by immunoaffinity chromatography using antibodies specific for SC2H. An immunoaffinity column is constructed by covalently coupling SC2H antibody to an activated chromatographic resin such as CnBr-activated Sepharose (Pharmacia Biotech). After the coupling, the resin is blocked and washed according to the manufacturer's instructions.

Cellular fractions from cells containing SC2H are prepared by solubilization of the whole cell and isolation of subcellular fractions by differential centrifugation, by the addition of detergent, or by other methods well known in the art. Alternatively, soluble SC2H containing a signal sequence may be secreted in useful quantity into the medium in which the cells are grown.

A fractionated SC2H-containing preparation is passed over the immunoaffinity column, and the column is washed under conditions that allow the preferential absorbance of SC2H (eg, high ionic strength buffers in the presence of detergent). The column is eluted under conditions that disrupt antibody/SC2H binding (eg, a buffer of pH 2–3 or a high concentration of a chaotrope such as urea or thiocyanate ion), and SC2H is collected.

XII Identification of Molecules Which Interact with SC2H

Labeled SC2H is useful as a research tool for identification, characterization and purification of molecules with which it interacts. In one embodiment of affinity purification, SC2H is covalently coupled to a chromatography column. Cells and their membranes are extracted, endogenous SC2H is removed and various SC2H-free subcomponents are passed over the column. SC2H-associated molecules bind to the column by virtue of their biological affinity. The SC2H-complex is recovered from the column, dissociated and the recovered molecule is subjected to N-terminal protein sequencing. This amino acid sequence is then used to identify the captured molecule or to design degenerate oligonucleotide probes for cloning its gene from an appropriate cDNA library.

In another alternate method, monoclonal antibodies are raised against SC2H and screened to identify those which inhibit the binding of labeled SC2H. These monoclonal antibodies are then used in affinity purification or expression cloning of associated molecules.

Other soluble binding molecules are identified in a similar manner. Labeled SC2H is incubated with extracts or biopsied materials derived from cells or tissues such as rheumatoid synovium, lung or cerebellum. After incubation, SC2H complexes (which are larger than the size of purified SC2H molecule) are identified by a sizing technique such as size exclusion chromatography or density gradient centrifugation and are purified by methods known in the art. The soluble binding protein(s) are subjected to N-terminal sequencing to obtain information sufficient for database identification, if the soluble protein is known, or for cloning, if the soluble protein is unknown.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

We claim:

1. An isolated and purified polynucleotide fragment encoding a polypeptide of SEQ ID NO: 1.

2. An isolated and purified polynucleotide sequence of claim 1 consisting of the sequence of SEQ ID NO:2.

3. A polynucleotide sequence fully complementary to the sequence of SEQ ID NO:2.

4. An expression vector containing a polynucleotide sequence of claim 1.

5. An isolated host cell comprising a polynucleotide sequence of claim 1.

6. A method for producing a polypeptide comprising the amino acid sequence shown in SEQ ID NO:1, the method comprising the steps of:

a) culturing the host cell of claim 5 under conditions suitable for the expression of the polypeptide; and b) recovering the polypeptide from the host cell.

* * * * *